US006596506B2

(12) United States Patent
Kim (10) Patent No.: US 6,596,506 B2
(45) Date of Patent: Jul. 22, 2003

(54) DOUBLE AND TRIPLE READOUT ASSAY SYSTEMS

(75) Inventor: Tae Kook Kim, Newton, MA (US)

(73) Assignee: President and Fellows of Harvard College ( * ) Notice: Subject to any disclaimer, the term of this patent is extended or adjusted under 35 U.S.C. 154(b) by 0 days.

(21) Appl. No.: 09/999,504

(22) Filed: Oct. 25, 2001

(65) Prior Publication Data

US 2002/0094517 A1 Jul. 18, 2002

Related U.S. Application Data

(60) Provisional application No. 60/243,689, filed on Oct. 27, 2000.

(51) Int. Cl.$^7$ .............................. C12Q 1/02; C12Q 1/00; C12N 15/85; C12N 15/00; C07H 21/04
(52) U.S. Cl. ...................... 435/29; 435/325; 435/320.1; 435/366; 435/6; 435/7.21; 435/8; 536/24.1
(58) Field of Search ............................. 435/325, 320.1, 435/366, 6, 7.21, 8, 29; 536/24.1

(56) References Cited

U.S. PATENT DOCUMENTS

| | | | |
|---|---|---|---|
| 5,283,179 A | 2/1994 | Wood | 435/8 |
| 5,641,641 A | 6/1997 | Wood | 435/8 |
| 5,650,289 A | 7/1997 | Wood | 435/8 |
| 5,670,356 A | 9/1997 | Sherf et al. | 435/189 |
| 5,726,025 A | 3/1998 | Kirschner et al. | 437/7.2 |
| 5,814,471 A | 9/1998 | Wood | 435/8 |
| 5,863,733 A | 1/1999 | Foulkes et al. | 435/6 |
| 5,939,266 A | 8/1999 | Kowalski | 435/6 |
| 5,972,621 A | 10/1999 | Tartaglia et al. | 435/7.1 |
| 5,976,793 A | 11/1999 | Foulkes et al. | 435/6 |
| 5,985,829 A | 11/1999 | Harris et al. | 514/12 |
| 6,007,998 A | 12/1999 | Rosenblum et al. | 435/7.1 |

FOREIGN PATENT DOCUMENTS

| | | |
|---|---|---|
| WO | WO 95/19367 | 7/1995 |
| WO | WO 97/24460 | 7/1997 |
| WO | WO 97/40379 | 10/1997 |
| WO | WO 00/47768 | 8/2000 |

OTHER PUBLICATIONS

Frank, "Spot–Synthesis: An Easy Technique for the Positionally Addressable, Parallel Chemical Synthesis on a Membrane Support" *Tetrahedron*, 48: 9217–9232, 1992.

Reddington, et al., "Combinatorial Electrochemistry: A Highly Parallel, Optical Screening Method for Discovery of Better Electrocatalysts" *Science*, 280: 1735–1737, 1998.

Bunin, et al., "The Combinatorial Synthesis and Chemical and Biological Evaluation of a 1,4–Benzodiazepine Library" *Proc. Natl. Acad. Sci. USA*, 91: 4708–4712, 1994.

Cinelli, et al., "The Enhanced Green Fluorescent Protein as a Tool for the Analysis of Protein Dynamics and Localization: Local Fluorescence Study at the Single–Molecule Level" *Photochem, Photobiol*, 71(6): 771–776, 2000.

De Wet, et al., "Cloning of Firefly Luciferase cDNA and the Expression of Active Luciferase in Escherichia Coli" *Proc. Natl. Acad. Sci. USA*, 82: 7870, 1985.

Dual–Luciferase ® Reporter 1000 Assay System.

Engebrecht, et al., "Measuring Gene Expression with Light", *Science*, 227: 1345, 1985.

Gennari, et al., "Combinatorial Libraries: Studies in Molecular Recognition and the Quest for New Catalysts" *Liebigs Ann./Recueil*, 637–647, 1997.

Geysen, et al., "A Priori Delineation of a Peptide Which Mimics a Discontinuous Antigenic Determinant" *Molec. Immunol.* 23: 709–715, 1996.

Houghton, et al., "Generation and Use of Synthetic Peptide Combinatorial Libraries for Basic Research and Drug Discovery" *Nature*, 354: 84–86, 1991.

Kiss–Toth, et al., "A Novel Mammalian Expression Screen Exploiting Green Fluorescent Protein–Based Transcription Detection in Single Cells" *J. Immunol. Methods* 239 (1–2): 125–135, 2000.

Miller, et al., "A Rapid and Sensitive Reporter Gene that Uses Green Fluorescent Protein Expression to Detect Chemicals with Estrogenic Activity", *Toxicol Sci*, 55(1): 69–77, 2000.

Molecular Cloning: A Laboratory Manual, $2^{nd}$ Ed., ed by Sambrook, Fritsch, and Maniatis (Cold Spring Harbor Laboratory Press: 1989.).

Nefzi, et al., "The Current Status of Heterocyclic Combinatorial Libraries" *Chem. Rev.* 97:449–472, 1997.

Sarver, et al., "Frontiers in HIV–1 Therapy: Fourth Conference of the NIAID National Cooperative Drug Discovery Groups–HIV" *AIDS Res. Hum. Retroviruses*, 8: 659–666, 1992.

(List continued on next page.)

Primary Examiner—James Ketter
Assistant Examiner—Daniel Sullivan
(74) Attorney, Agent, or Firm—Choate, Hall & Stewart; Brenda H. Jarrell; C. Hunter Baker (57) ABSTRACT

The present invention provides assays for identifying compounds that affect the transcriptional activity of a protein of interest or affect the stability of the protein of interest. The triple readout assay system which can be used to identify compounds that affect the transcriptional activity of a protein of interest uses three cell lines to control for non-specific effects such as sequences flanking the inserted gene and cytotoxicity. The double readout assay system assesses protein stability and uses a fusion protein of a reporter and the protein of interest. These assay systems may be particularly useful in identifying compounds that affect transcription factors and tumor suppressors. In a particular embodiment, the tumor suppressor p53 is the target protein being studied.

32 Claims, 5 Drawing Sheets

OTHER PUBLICATIONS

Tan, et al., "Stereoselective Synthesis of Over Two Million Compounds Having Structural Features Both Reminiscent of Natural Products and Compatible with Miniaturized Cell–Based Assays", *J. Am. Chem. Soc.*, 120: 8565, 1998.

Thompson, et al., "Synthesis and Applications of Small Molecule Libraries"*Chem. Rev.* 96: 555–600, 1996.

Witvrouw, et al., "Cell Type–Specific Anti–Human Immunodeficiency Virus Type 1 Activity of the Transactivation Inhibitor Ro5–3335" *Antimicrob. Agents Chemother*, 36: 2628–2633, 1992.

Yang, et al., "Identification of a Novel Inhibitor of Nuclear Factor–KappaB, RelA–Associated Inhibitor", *J. Biol. Chem*, 28: 274(22): 15662–15670, 1999.

Kim, et al., "Signaling Pathways to the Assembly of an Interferon–βEnhanceosome", The Journal of Biological Chemistry, 275(22):16910–16917, 2000.

Kim, T., "A Vitro Transcriptional Activation of p21 Promoter by p53", *Biochemical and Biophysical Research Communications*, 234: 300–302, 1997.

Kim, et al., "Chemotherapeutic DNA–Damaging Drugs Activate Interferon Regulatory Factor–7 by the Mitogen–Activated Protein Kinase Kinase–4–c–Jun $NH_2$–Terminal", *Cancer Research*, 60: 1153–1156, 2000.

International Search Report issued for corresponding PCT application PCT/US01/5124.

Multiple (Triple and Double) Readout in One Assay Well

Facilitates Identification of Chemicals that Specifically Affect p53 Function without Affecting Control Gene Function Increases Screening Efficiencies by Eliminating Multiple Screenings

DOUBLE AND TRIPLE READOUT ASSAY SYSTEMS

RELATED APPLICATIONS

The present application claims priority to co-pending provisional application, U.S. Ser. No. 60/243,689, filed Oct. 27, 2000, which is incorporated herein by reference.

BACKGROUND OF THE INVENTION

Pharmaceutical screens and biological assays have been used for decades in the pharmaceutical and biotech industries to identify lead compounds in the search for new pharmaceutical agents. In the last decade, the chemist's ability to synthesize large numbers of chemical compounds in a short amount of time through techniques such as combinatorial chemistry has greatly increased (for a recent review of the area of combinatorial chemistry, please see Geysen et al. *Molec. Immunol.* 23:709–715, 1986; Houghton et al. *Nature* 354:84–86, 1991; Frank *Tetrahedron* 48:9217–9232, 1992; Bunin et al. *Proc. Natl. Acad. Sci. USA* 91:4708–4712, 1994; Thompson et al. *Chem. Rev.* 96:555–600, 1996; Keating et al. *Chem. Rev.* 97:449–472, 1997; Gennari et al. *Liebigs Ann./Recueil* 637–647, 1997; Reddington et al. *Science* 280:1735–1737, 1998; each of which is incorporated herein by reference), and it has expanded beyond the capacity of traditional screening methods. Often, thousands to millions of compounds need to be screened to identify those having a desired pharmaceutical property (e.g., anti-neoplastic activity, immunosuppressive activity, etc.). Many of the currently available screens are biochemical assay systems in which a compound is added to a purified or partially purified cell extract to see if it possesses the desired activity. In contrast to the biochemical assay systems, currently available cell-based assay systems identify bioactive molecules that are cell-permeable and work within physiological environments. However, one of the major drawbacks to cell-based assay screens is the high false-positive rate resulting from non-specific effects of the compound within the cell (for examples, please see Sarver et al. *AIDS Res. Hum. Retroviruses* 8:659–666, 1992; Witvrouw et al *Antimicrob. Agents Chemother.* 36:2628–2633, 1992; each of which is incorporated herein by reference). Given the fundamental importance of gene regulation in many disease states, one typical cell-based assay measures the activity of a reporter gene under the control of a specific reporter. However, inhibition of reporter gene expression does not necessarily indicate a specific interference with promoter activity but could reflect a non-specific inhibition of cellular functions, for example due to cytotoxicity.

One particularly important protein in the study of cancer is the nuclear phosphoprotein, p53. p53 is thought to be mutated in over 50% of human cancers. Mutations in the p53 gene have been found in tumors of colon, lung, breast, ovary, bladder, and several other organs. When mutant forms of the p53 gene are introduced into primary fibroblasts, these cells become immortalized. The wild type p53 gene has been shown to suppress the growth of transformed human cells, but oncogenic forms of p53 lose this suppressor function. Therefore, the p53 gene has been termed a "tumor suppressor" gene. Given the role of p53 in tumorigenesis, it has become an important potential target in the search for new anti-neoplastic agents.

The wild type p53 may be interfered with functionally. For example, a transforming viral infection of the cell can interfere with p53 protein product. For instance, certain strains of human papillomavirus (HPV) are transforming and are known to interfere with the level of p53 protein in the infected cell because the virus produces a protein, E6, which promotes degradation of the p53 protein.

There is also an interest in p53 because p53 protein is capable of inducing apoptosis in certain cells. In apoptosis, or "programmed cell death", a series of lethal events for the cell appear to be generated directly as a result of transcription of cellular DNA. For example, lymphocytes exposed to glucocorticoids die by apoptosis. Involution of hormone sensitive tissue such as breast and prostate that occurs when the trophic hormone is removed occurs via apoptosis.

In particular, recent studies have indicated that the introduction of wild type (non-mutated) p53 into transformed cell lines that carry a mutant form of p53 induces the cells to undergo apoptosis with disintegration of nuclear DNA. It is believed that p53 may suppress tumor development by inducing apoptosis, thus modulating cell growth.

Given the importance of p53 in a variety of physiological and disease states, there is a need for cell-based assays with low backgrounds that could be used in screening compounds to identify inhibitors and activators of p53. Moreover, both the rapid increase of new drug targets through genomics research and the availability of vast libraries of chemical compounds create an enormous demand for new technologies which would improve the screening process.

SUMMARY OF THE INVENTION

The present invention provides assay systems for screening chemical compounds to identify activators and inhibitors of proteins of interest (e.g., transcription factors, enzymes, and tumor suppressors).

In one aspect, the invention provides a cell-based triple readout assay system for identifying compounds that affect transcriptional activity. Three separate cell lines, each containing a different engineered construct, are used. Two have been transfected with a construct comprising a reporter gene and a modulatable transcriptional regulatory sequence known to bind a selected transcription factor. Each of the two cell lines has a different reporter gene, and the construct is integrated into the genome in a different location to control for the effect of flanking sequences on the transcription of the reporter gene. A third cell line has been transfected with a construct comprising a third reporter gene operably linked to a constitutive promoter. The third cell line is used to assess general cytotoxicity of the test compound. At least one cell derived from each of the three cell lines is contacted with the test compound, and the levels of the reporter genes are assayed and used to determine the specificity of the test compound on the transcription factor or transcription factor pathway. In a particularly preferred embodiment, the transcription factor of interest is p53.

In another aspect, the invention provides a cell-based double readout assay system for identifying compounds that affect protein stability/levels in cells. A fusion protein is created between a protein of interest and a first reporter protein. The fusion protein and a second reporter protein are expressed in a cell line to which the test compound is added. The second reporter protein is used to control for non-specific effects such as cytotoxicity. The levels of the two proteins (i.e., the fusion protein and the second reporter protein) are measured to assess the specificity of the test compound on the protein of interest. In a particularly preferred embodiment, the two proteins are translated from the same mRNA transcript of an engineered DNA construct.

In a particularly preferred embodiment of this aspect of the present invention, the protein of interest is p53. One critical point of regulation of p53 occurs at the protein level. Tumor mutations that affect its conformation typically increase its half-life, in part by inhibiting its degradation by the ubiquitin-proteasome pathway. Consistent with its critical role in tumor suppression, many oncoproteins including human papillomavirus E6 oncoprotein target the p53 protein and alter its stability.

In yet another aspect, the invention provides chemical inhibitors and activators of p53. Such inhibitors and activators may preferably be identified and/or characterized using one or both of the inventive triple and double readout assay systems. In certain clinical situations, it is desirable to suppress the cellular effects of p53. For example, p53-dependent apoptosis is thought to contribute to the toxic side effects of anti-cancer treatment with chemotherapy. In certain preferred embodiments of the invention, the p53 inhibitors or activators are provided in the context of a pharmaceutical composition. In a preferred embodiment, the inhibitors and activators are small molecules.

In another aspect, the invention provides kits for performing the double and triple readout assays. Preferably, an inventive kit contains all the reagents needed to assay a test compound for its effect on transcription and/or protein stability/levels. In a particularly preferred embodiment, a kit to be used in performing the triple readout assay contains the three cell lines described above. A kit for performing the double readout assay preferably contains a cell line stably transfected with a fusion protein and a second reporter protein. In another preferred embodiment, an inventive kit comprises DNA constructs to be used in transfecting a cell line. Preferred inventive kits may also contain additional reagents such as media for growing the cells, enzyme substrates (e.g., the substrate of luciferase), DNA damaging compounds (e.g., adriamycin), human papillomavirus E6 oncoprotein, growth factors, etc.

Definitions

Unless indicated otherwise, the terms defined below have the following meanings:

"Compound": The term "compound" or "chemical compound" as used herein can include organometallic compounds, polynucleotides, oligonucleotides, peptides, proteins, organic compounds, metals, transitional metal complexes, and small molecules. In a particularly preferred embodiment, the term compound refers to small molecules (e.g., preferably, non-peptidic and non-oligomeric) and excludes peptides, polynucleotides, transition metal complexes, metals, and organometallic compounds.

"Constitutive promoter": The term constitutive promoter refers to a promoter that is always "on". In other words, genes operably linked to a constitutive promoter are always being transcribed to produce mRNA.

"Construct": The term construct refers to any polynucleotide that has been manipulated by the hand of man. Specifically, the construct is isolated from other sequences that are found in the natural state. The construct may be produced by recombinant known in the art such as the polymerase chain reaction. Preferably, the polynucleotide contains various elements that are operably linked, and the construct is introduced into a cell. For example, the construct may contain a promoter operably linked to a coding sequence, and the construct may be introduced into a cell to cause the cell to produce the encoded protein. In a preferred embodiment, the construct has been created or engineered by the hand of man and does not occur naturally.

"Fusion protein": The term "fusion protein" refers to a protein comprising two or more polypeptides that, although typically unjoined in their native state, are joined by their respective amino and carboxyl termini through a peptide linkage to form a single continuous polypeptide. The two or more polypeptide components can be either directly joined or indirectly joined through a peptide linker/spacer. The fusion protein may be translated by a ribosome from mRNA as a single polypeptide, or the polypeptides may be joined using synthetic or enzymatic chemistry.

"Modulatable transcriptional regulatory sequence": The term "modulatable transcriptional regulatory sequence" refers to a DNA sequence capable of regulating the initiation of transcription from the promoter of the reporter gene by the binding of a protein to the sequence. The protein preferably binds a regulatory sequence of the construct in which the promoter, modulatable transcriptional regulatory sequence, and reporter gene are operably linked, and thereby the protein either up-regulates or down-regulates the transcription from the promoter.

"Operably linked": The term operably linked refers to two segments of polynucleotide sequence that can affect each other. In a particularly preferred embodiment, one of the two segments is a sequence that binds a protein (e.g., polymerase, enhancer, and transcription factor), and the binding of the protein to the sequence leads to the transcription of a gene sequence located in the second segment. In another particularly preferred embodiment, the binding of a molecule (e.g., nucleic acid, small molecule, protein, and peptide) to one segment may inhibit or enhance the binding of another molecule (e.g., nucleic acid, small molecule, protein, and peptide) to the second segment. Preferably, two operably linked segments are covalently linked, but any type of association sufficient to achieve the desired results is considered to be operably linked in the context of the present invention.

"p53": The term "p53" as used in the present invention refers to both the gene and protein form of p53 or any homolog of p53 or member of the family of p53 genes. The homolog should be at least 50% homologous to the mouse p53 DNA or protein sequence; preferably, at least 60% homologous, and most preferably, greater than 75% homologous. A homolog of p53 may also be identified by its activity such as its ability to suppress the growth of transformed cells. In another preferred embodiment, the homolog of p53 is identified by its location in the genome (e.g., location on the chromosome). In yet another preferred embodiment, the homolog of p53 is able to hybridize to the p53 gene under standard hybridization conditions. p53 may also refer to a fragment of a p53 gene. In certain preferred embodiments, p63, p73, and homologs thereof are considered to be p53 family members. In other preferred embodiments, homologs are at least 50% homologous within the central sequence-specific DNA binding domain, the N-terminal transactivation domains, and/or the C-terminal oligomerization domain, more preferably greater than 60% homologous.

"p53 binding element": The term "p53 binding element" refers to a sequence of a polynucleotide that binds the p53 protein. In a preferred embodiment, the p53 binding element is the p53 binding element found in the p21, bax, or 14-3-3 gene. The p53 binding element may comprise multiple binding elements (i.e., be multimerized).

"Polynucleotide" or "oligonucleotide": Polynucleotide or oligonucleotide refers to a polymer of nucleotides. Preferably, the polynucleotide comprises at least three nucleotides, more preferably it comprises at least 10 nucleotides, and most preferably it comprises at least 100 nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g, 2'-fluororibose, ribose, 2'-deoxyribose, arabinose, and hexose), or modified phosphate groups (e.g., phosphorothioates and 5'-N-phosphoramidite linkages).

"Protein": According to the present invention, a "protein" comprises a polymer of amino acid residues linked together by peptide bonds. The term, as used herein, refers to proteins, polypeptides, and peptides of any size, structure, or function. Typically, a protein will be at least three amino acids long. Peptide may refer to an individual peptide or a collection of peptides. Inventive peptides preferably contain only natural amino acids, although non-natural amino acids (i.e., compounds that do not occur in nature but that can be incorporated into a polypeptide chain;) and/or amino acid analogs as are known in the art may alternatively be employed. Also, one or more of the amino acids in an inventive peptide may be modified, for example, by the addition of a chemical entity such as a carbohydrate group, a phosphate group, a hydroxyl group, a farnesyl group, an isofarnesyl group, a fatty acid group, a linker for conjugation, functionalization, or other modification, etc. A protein may also be a single molecule or may be a multi-molecular complex. A protein may be a fragment of a naturally occurring protein or peptide. A protein may be naturally occurring, recombinant, or synthetic, or any combination of these.

"Reporter gene": As used herein, the term "reporter gene" refers to a gene whose transcript or any other gene product (e.g., protein) is detectable. Preferably, the gene product is also quantifiable. More preferably, the gene product is detectable using a standard assay. Most preferably, the gene product is detectable using a standard assay for which the reagents used in the assay are available in a kit. In certain preferred embodiments, the reporter gene encodes a fluorescent protein or an enzyme whose activity is detectable and preferably quantifiable.

"Small Molecule": As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon—carbon bonds, and has a molecular weight of less than 1500, although this characterization is not intended to be limiting for the purposes of the present invention. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" *J. Am. Chem. Soc.* 120:8565, 1998) and pending application Ser. No. 08/951,930 "Synthesis of Combinatorial Libraries of Compounds Reminiscent of Natural Products", the entire contents of which are incorporated herein by reference.

DESCRIPTION OF THE DRAWING

FIGS. 1A and B show the transcriptional activation of p53 binding sites. (A) Six copies of p53 binding sites from p21, bax, and 14-3-3 gene, and (B) multiple copies (3, 6, and 12) of the p53 site from 14-3-3 gene were cloned upstream of FL (firefly luciferase) reporter gene. RKO cells were transfected with these plasmids and reporter activities were analyzed after treatment with adriamycin. The results are presented as fold induction, compared to the luciferase activities from cells untreated with adriamycin.

FIG. 4 shows triple readout for p53 transcriptional activity. An equal number of each of the three different RKO reporter cell lines (containing FL and SEAP under the control of p53, an RL under the control of the CMV promoter) was cultured in each well of 384-well plates. Chemicals were transferred into the wells using pin arrays and preincubated with cells before addition or adriamycin (0.5–1.0 μM). After ~24 hours, SEAP activity was determined from culture media using the SEAP Assay System (Promega). FL and RL activities were determined from cell lysates using the Dual Luciferase Assay System (Promega). In the screens, we identified chemicals that specifically affected p53-dependent FL and SEAP expression, without affecting CMV promoter-driven RL expression.

FIGS. 5A and B show stabilization of p53 protein by DNA damaging agents and destabilization of p53 protein by E6 oncoprotein. (A) p53-FL (firefly luciferase) and RL (renilla luciferase) reporter activities were determined in the selected MCF7 clone before and after treatment with adriamycin. The results are presented as fold induction (p53-FL/RL), compared to the luciferase activities from cells untreated with adriamycin. (B) p53-FL and RL reporter activities were determined in the selected MCF7 clone in the absence or presence of expression of E6 oncoprotein. The results are presented as fold induction (p53-FL/RL), compared to the luciferase activities from untreated cells.

FIG. 7 shows the double readout assay for p53 protein stability. A 384-well plate was used to culture MCF7 cells expressing p53-FL and RL proteins, both under control of the CMV promoter. Chemicals were transferred into 384-well plates using pin arrays and preincubated with cells before addition of adriamycin (1 $\mu$M). After ~24 hours, p53-FL and RL activities were determined from cell lysates using the Dual Luciferase Assay System (Promega). In the screens, chemical compounds were identified that specifically affect the stability/levels of p53-FL protein, without affecting those of the RL protein.

FIGS. 8A and B shows specific chemicals identified from multiple readouts. (A) The triple and double readout systems were effectively used to screen specific chemicals in a diverse collection of 16,320 synthetic chemicals (Chembridge Corporation), which affect the transcriptional activity and protein stability of p53, respectively. (B) Shown in an example of the selected chemicals which affected p53-dependent FL and SEAP expression, without affecting CMV promoter-driven RL expression.

FIG. 9 shows double and triple readouts for signaling pathways as a drug-discovery platform. Using multiple readouts, these assays can be used to effectively screen for small molecules specific to p53. Some chemicals may affect transcriptional activity of p53 by up-regulating or down-regulating p53 protein levels. The other chemicals, those whose activity was detected in the triple readout, but not the double readout, presumably modulate p53 transcriptional activity without affecting p53 protein stability. Thus, these readouts enabled us to select and categorize chemicals with potent and specific effects on p53 protein stability and/or transcriptional activity. These assay systems lay out the basis of systematic screening for specific chemical ligands in many other signaling pathways.

DESCRIPTION OF CERTAIN PREFERRED EMBODIMENTS

The present invention provides systems for identifying inhibitors and activators of genes and gene products using cell-based assays with built-in controls to minimize the number of non-specific hits (i.e., background). The inventive assay systems eliminate the need for multiple screenings, which can be costly and time-consuming. The inventive assays determine the effect of a test compound on transcription and levels/stability of the protein of interest.

Triple Readout Assay System

The present invention provides a cell-based triple readout assay system that involves the measurement of the activity or level of a reporter gene product under the control of a specific promoter. Past efforts to assay reporter gene activity were complicated by problems including non-specific inhibition of reporter gene expression, which could be due to non-specific inhibition of cellular functions by cytotoxicity. Before the present invention, in order to distinguish between "true" inhibition and other non-specific effects, a number of time-consuming and costly experiments would need to be performed. Also, another problem associated with many available reporter gene assays is that upon integration of the reporter gene into the genome the transcription of the reporter gene could be influenced by DNA sequences around which the reporter gene was stably inserted.

The inventive triple readout assay overcomes these limitations and therefore reduces or eliminates the need for multiple screenings. The inventive cell-based triple readout assay involves three separate cell lines. Two of the cell lines express a reporter gene under the control of the same modulatable transcriptional regulatory sequence. The third cell line expresses a reporter gene under the control of a constitutive promoter. The influence of the DNA sequences adjacent to where the reporter gene was stably inserted is controlled for by the first two cell lines. General effects of cytotoxicity or inhibition of gene expression are eliminated using the third cell line that uses a constitutive promoter.

In a particularly preferred embodiment, the transcription factor being studied is p53. In unstressed cells, p53 is present at low levels and exists in a latent, inactive form. Levels and/or activity of p53 increase in response to a variety of stimuli including genotoxic stress. Active p53 protein accumulates in the nucleus, binding to its responsive DNA elements and inducing the transcription of its target genes. Under inappropriate growth conditions, p53 can integrate a variety of signals to the specific gene regulation for protection of cells against neoplastic transformation. Consistent with its critical role in tumor suppression, the majority of the p53 mutations associated with human tumors, in addition to many oncoproteins, decrease p53's sequence-specific DNA binding and transcriptional activity. Thus, small molecules that modulate transcriptional activity of p53 are important for therapeutic purposes.

Any cell line may be used in developing the cell lines used in the inventive triple readout assay. The cells may be animal, plant, bacterial, or fungal cells. In a preferred embodiment, the cell line is a mammalian cell line. In a particularly preferred embodiment, the cell line is a human cell line. The chosen cell line may satisfy other requirements particular to the protein of interest and known to one of skill in this art; for example, if one were interested in regulating p53-dependent transcription, the cell line should preferably (1) express wild-type p53; (2) show a high level of induction of p53 after treatment with DNA damaging agents; and/or (3) have functionally intact p53-mediated growth arrest pathways. A particularly preferred cell line used in studying p53 is the RKO cell line, a colon cancer cell line. Those of ordinary skill in this art will readily appreciate the multitude of cell lines that could be utilized in the assay systems and would be able to choose a cell line based on multiple factors affecting the gene or protein being studied in the inventive assay.

The modulatable transcriptional regulatory sequence is modulated by the protein of interest or by a protein which is secondarily or indirectly modulated by the protein of interest. In some embodiments, the protein of interest directly modulates transcription by binding to the regulatory sequence directly or indirectly. In other embodiments, the protein of interest acts indirectly to modulate transcription. The protein of interest may act indirectly through a single-or multi-step biological pathway. The responsiveness of the regulatory sequence may depend on the presence or absence, or activity level, of the protein of interest.

To give but one example, in which p53 is the protein of interest, the modulatable transcriptional regulatory sequence comprises at least one p53 binding element. Any p53 binding element may be operably linked to the reporter gene. In a preferred embodiment, the p53 binding element shows a high level of induction of the operably linked reporter gene in response to DNA damage. Examples of p53 binding elements can be found in the following three target genes: p21, bax, and 14-3-3. In a particularly preferred embodiment, the p53 binding element is multimerized. For example, six to twelve copies of the element may result in nearly saturated levels of p53 induction. In other embodiments, the p53 may act as a repressor, and down-regulation of the reporter gene is assayed.

The reporter gene may encode any gene product (i.e., transcript and protein) that is detectable by any known method (e.g., Northern analysis, Western analysis, radio-immuno assay, enzymatic assay, change in fluorescence, change in absorbance, etc.), and preferably the level of the gene product is quantifiable by any known method (please see, *Molecular Cloning: A Laboratory Manual,* 2nd Ed., ed. by Sambrook, Fritsch, and Maniatis (Cold Spring Harbor Laboratory Press: 1989); *Nucleic Acid Hybridization* (B. D. Hames & S. J. Higgins eds. 1984); the treatise, *Methods in Enzymology* (Academic Press, Inc., N.Y.); *Immunochemical Methods in Cell and Molecular Biology* (Mayer and Walker, eds., Academic Press, London, 1987); Ausubel et al. *Current Protocols in Molecular Biology* (John Wiley & Sons, Inc., New York, 1999); *Transcription and Translation* (B. D. Hames & S. J. Higgins eds. 1984); *Handbook of Experimental Immunology,* Volumes I–IV (D. M. Weir and C. C. Blackwell, eds., 1986); each of which is incorporated herein by reference). In a preferred embodiment, the reporter gene is an enzyme (e.g., kinases, phosphatases, luciferases, β-galactosidase, reductases, synthases, horseradish peroxidase, synthetases, etc.). The enzyme itself may be detectable or the activity of the enzyme may be used to indirectly measure the level of the enzyme.

In a particularly preferred embodiment of the present invention, at least one of the reporter genes of the assay system encodes a luciferase protein. Luciferases may come from any organism including the North American firefly, *Photinus pyralis,* the sea pansy, *Renilla reniformis,* and the bacterium, *Vibrio fischeri.* A more complete description of luciferases and their use as transcriptional reporters can be found in De Wet et al. ("Cloning of firefly luciferase cDNA and the expression of active luciferase in *Escherichia coli*" *Proc. Natl. Acad. Sci. USA* 82:7870, 1985; incorporated herein by reference) and Engebrecht et al ("Measuring gene expression with light" *Science* 227:1345, 1985; incorporated herein by reference).

In another particularly preferred embodiment of the present invention, at least one of the reporter genes of the assay system encodes an alkaline phosphatase. The phosphatase gene may be from any species. A particularly preferred alkaline phosphatase is secreted alkaline phosphatase (SEAP).

In another particularly preferred embodiment, the reporter gene encodes an enhanced green fluorescent protein (EGFP). For more details in the use of enhanced green fluorescent protein as a reporter, please see Cinelli et al. (*Photochem. Photobiol.* 71(6):771–776, 2000; incorporated herein by reference); Kiss-Toth et al. (*J. Immunol Methods* 239(1–2):125–135, 2000; incorporated herein by reference); and Millet et al. (*Toxicol. Sci.* 55(1):69–77, 2000; incorporated herein by reference).

Double Readout Assay System

The level of certain proteins in the cell regulates many cellular processes. Therefore, the degradation, stability, and accumulation of proteins are highly controlled in the cell. For example, one pathway which regulates the degradation of proteins is the ubiquitin-proteasome pathway. The ability to regulate specific protein degradation pathways or to affect the stability of specific proteins would allow for a new approach in treating diseases such as cancer, autoimmune diseases, and neurological diseases.

Traditional assays for identifying compounds that effect protein stability have been hampered by the large number of non-specific effects. For example, an increase in protein stability may reflect a non-specific inhibition of cellular functions by the cytotoxic effect of the compound rather than a specific effect on the protein's stability.

To give but one example of a protein whose level is critical in a cellular process, p53 is a tumor suppressor protein whose level has been found to be important in tumorigenesis. Mutations in p53 that affect its conformation typically increase its half-life, in part by inhibiting its degradation by the ubiquitin-proteasome pathway. In unstressed cells, p53 is present at low levels and exists in a latent, inactive form. If the cell is then stressed (e.g., genotoxic stress), the levels and/or activity of p53 increase. Active p53 protein then accumulates in the nucleus of the cell, binds to its responsive DNA elements, and induces the expression of its target genes. Under inappropriate growth conditions, p53 can integrate a variety of signals for protection of the cells against neoplastic transformation. Consistent with p53's critical role in tumor suppression, many oncoproteins target p53 and its protein stability, including the human papillomavirus E6 oncoprotein. Therefore, compounds that could modulate p53 protein stability are important for therapeutic purposes.

In the inventive double readout assay system, the protein of interest (e.g., p53) is fused to a first reporter protein, for example using standard recombinant DNA techniques (Ausubel et al., *Current Protocols in Molecular Biology* (John Wiley & Sons, Inc., New York, 1999); Sambrook, Fritsch, and Maniatis, eds., *Molecular Cloning: A Laboratory Manual,* $2^{nd}$ ed., (Cold Spring Harbor Laboratory Press, 1989); each of which is incorporated herein by reference). Both the fusion protein and a control reporter protein are expressed in the cell. The cell(s) are contacted with various test compounds, and the levels of the fusion protein and the control reporter protein are measured. The level of the fusion protein when compared to the level of the control reporter protein would allow for the identification of compounds specifically affecting the stability of the protein of interest due to their effects on the ratio of fusion protein to control. In a preferred embodiment, at least a 50% change in the level of the fusion protein when compared to that of the control reporter protein is considered to be a hit, more preferably there is at least a 150% change, and most preferably there is at a 500% change.

The reporter proteins may be any protein or peptide as described above in the triple readout assay system. Preferably, the presence of the protein or peptide can be detected using standard techniques (e.g., radioimmunoassay, radio-labeling, immunoassay, assay for enzymatic activity, absorbance, fluorescence, luminescence, and Western blot). More preferably, the level of each of the reporter proteins is easily quantifiable using standard techniques even at low levels. In a preferred embodiment, the reporter proteins are related so that their levels are easily comparable.

In a particularly preferred embodiment, the reporter proteins are luciferases as described above in the triple readout assay system. Preferably, the luciferases are distinguishable from one another if two luciferases are used as the reporter proteins. In a particularly preferred embodiment, one reporter protein is firefly luciferase (FL) from *Photinus*

*pyralis,* and the other is Renilla luciferase (RL) from *Renilla reniformis.* The protein levels may be determined using the Dual-Luciferase® Assay System (Promega) (*Dual-Luciferase® Reporter* 1000 *Assay System,* Technical Manual No. 046, Promega Corp., Madison, Wis., 1999; incorporated herein by reference).

Preferably, the genes encoding the fusion protein and the control reporter protein are transcribed at substantially the same level. In a particularly preferred embodiment, the two genes of the proteins are transcribed together to create one transcript. An internal ribosome entry site (IRES) may be inserted between the two genes to ensure translation of both encoded proteins. In another particularly preferred embodiment, the two genes are under the control of the same promoter sequences and regulatory elements.

As with the inventive triple readout assay system, any cell line in which the proteins are expressed may be employed in the inventive double readout system. Preferably, in the example of p53, the cell line contains active p53 turnover pathways, the steady-state level of p53 protein is relatively low, and the level of p53 protein significantly increases following stress stimuli (e.g., treatment with chemotherapeutic DNA damaging agents). In a particularly preferred embodiment, the cell line is MCF7.

In another particularly preferred embodiment, the cell line is transfected with the fusion protein gene and the control reporter gene, and the resulting cells are tested for stabilization of p53 protein after treatment with adriamycin. Preferably, the clones show a 5-fold increase in the level of the fusion protein. More preferably, the clones show a 10-fold increase; and most preferably, the clones show a 20-fold increase.

The cell line may be transfected with other genes that affect p53 degradation. In a particularly preferred embodiment, the cell line is transfected with the human papillomavirus oncoprotein E6. Many other oncoproteins may be used in this embodiment of the invention. As will be appreciated by one of skill in this art, any gene that may affect the stability/level of the protein being investigated may be transfected into the cell line.

Test Compounds

The compounds to be screened in the inventive double and triple readout assays may be provided by any means known in the art. The test compounds may be polynucleotides, peptides, proteins, small molecules, organic molecules, inorganic molecules, peptidomimetics, antibodies, or other chemical compounds. The compounds may be prepared by purification or isolation from a source (e.g., plant, fungus, animal, bacteria, soil sample, etc.), or by synthesis. The synthesized compounds may be created by more conventional one-by-one synthetic methods or by combinatorial chemistry methods through rapid parallel and/or automated synthesis. The compounds may be provided in crude or pure forms. The compounds may be natural products or derivatives of natural products. In another preferred embodiment, the compounds are provided from the historical compound files of large pharmaceutical and chemical companies. Preferably, the compounds are provided as libraries of chemical compounds.

The compounds are screened by the methods described above to identify activators and inhibitors of the protein/gene of interest. To give but one example, the methods may be used to identify activators and inhibitors of p53. Chemical inhibitors of p53 are useful in preventing or minimizing the toxic side effects derived from p53-dependent apoptosis (e.g., those side effects seen in individuals undergoing chemotherapy and radiation therapy). Chemical activators of p53 would be useful in developing new anti-neoplastic agents. In a particularly preferred embodiment, the compounds may activate or inhibit the protein/gene of interest by two-fold, more preferably five-fold, and most preferably ten-fold.

Kits

The present invention also provides kits for performing the double and triple readout assays. Preferably, these kits include all the reagents necessary to assay a test compound or library of test compounds. The kits may include cell lines, stably transfected cell lines as described above, media, growth factors, DNA damaging agents (e.g., bleomycin, adriamycin), human papillomavirus E6 oncoprotein, DNA constructs, enzyme substrate (e.g., substrate of the luciferase enzyme being assayed for), etc.

These and other aspects of the present invention will be further appreciated upon consideration of the following Examples, which are intended to illustrate certain particular embodiments of the invention but are not intended to limit its scope, as defined by the claims.

EXAMPLES

Example 1—Triple Readout for p53 Transcriptional Activity

Figure 1A:
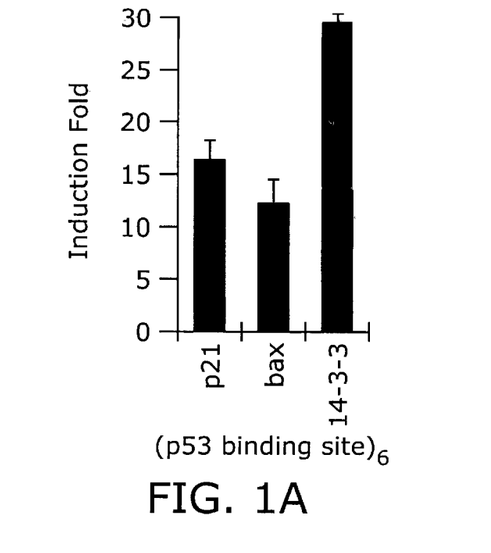
Figure 1B:
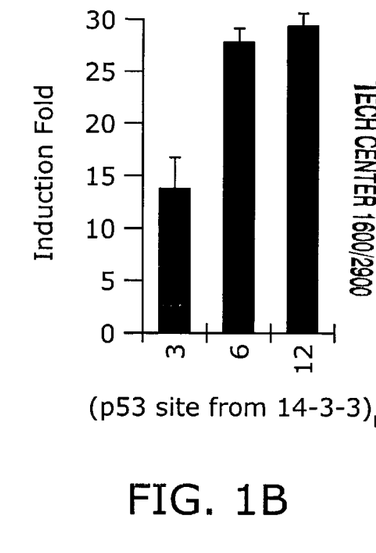
Figure 2:
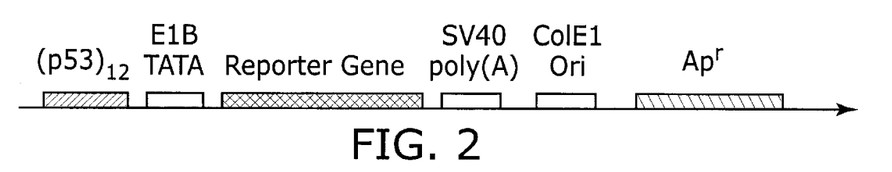
FIG. 2 shows a reporter plasmid used for p53 transcriptional activity. Twelve copies of the p53 site from 14-3-3 gene were cloned upstream of FL (firefly luciferase) or SEAP (secreted alkaline phosphatase) reporter gene. This reporter plasmid was used to monitor the transcriptional activity of p53 in cells.
Figure 3:
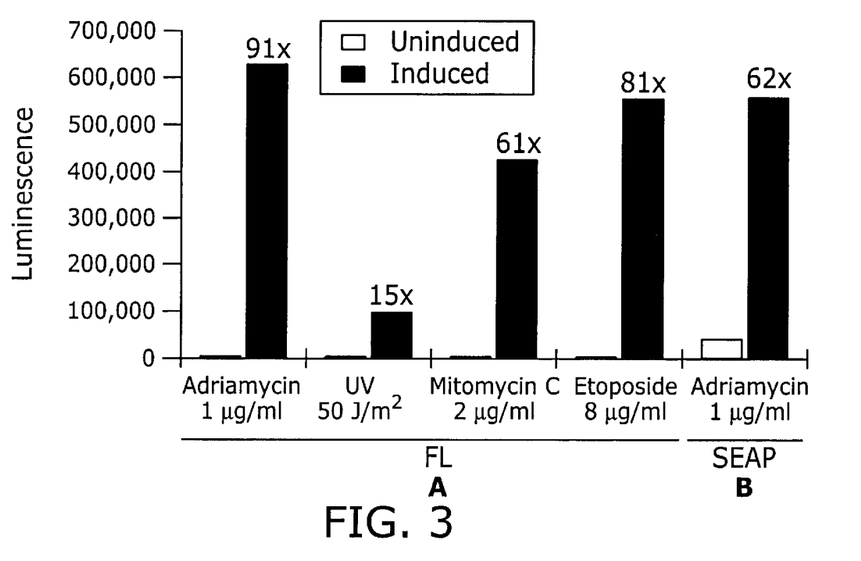
FIG. 3 shows transcriptional activation of p53 in a selected stable cell line by DNA damaging agents. (A) FL (firefly luciferase) and (B) SEAP (secreted alkaline phosphatase) reporter activities were determined in the selected clone of stably transfected RKO cells before and after treatment with various DNA damaging agents (adriamycin, UV radiation, mitomycin C, and etopside). The results are presented as fold induction, compared to the reporter activities from untreated cells.
Figure 4:
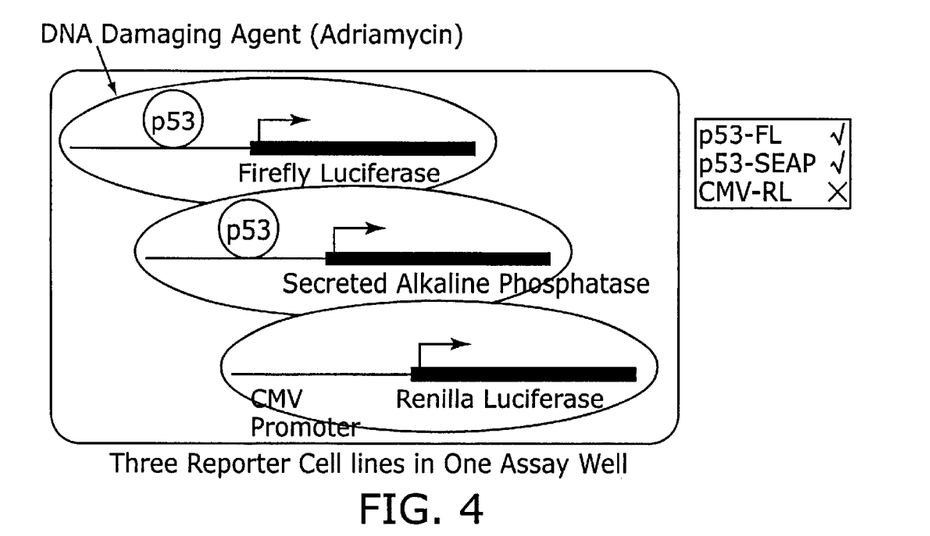
Figure 5A:
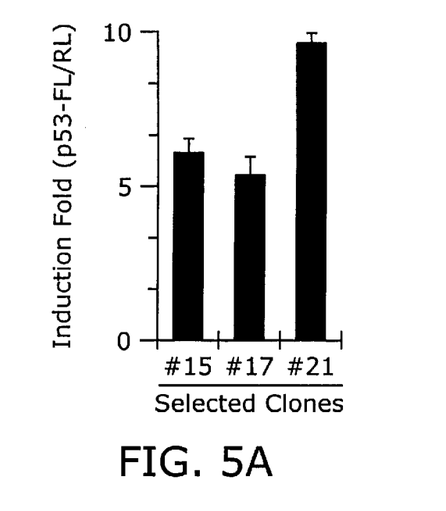
Figure 5B:
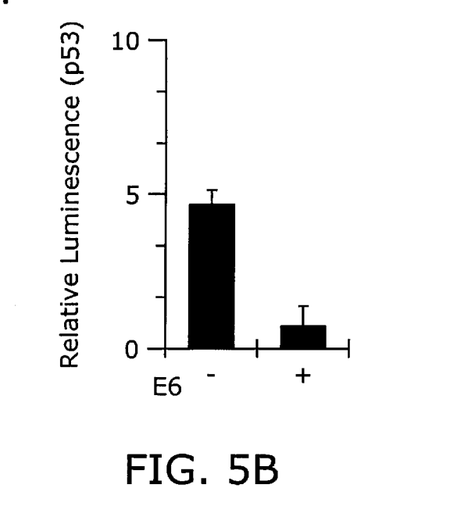

Three different reporter cell lines (one containing FL under the control of p53, a second containing SEAP under the control of p53, and a third containing RL under the control of the CMV promoter) were established by selection with hygromycin (400 µg/mL) after transfection of RKO cells with the reporter plasmid (see FIG. 2). In the screen, cells derived from the three cell lines were mixed, and the activities of the three different reporter proteins were assayed in a single well after incubation with chemicals as described below.

The cells lines were maintained in McCoy media supplemented with antibiotics and 10% heat-inactivated fetal bovine serum (FBS) to exclude SEAP activity in the serum. After monomerization of reporter cells with trypsin, an equal number of cells from each of the three cells lines was mixed in a flask, and 30 µL of the resulting cell mixture was dispensed in each well of a 384-well plate ($5 \times 10^3$ cells/well) using an automatic dispenser (Multidrop 384, Labsystems). After 12–16 hours, test chemical compounds were introduced into the wells using pin arrays resulting in a final concentration of ~5 µg/mL of the test compound and pre-incubated with the cells for 2 hours followed by the addition of adriamycin (0.5–1.0 µM). After 24 hours, activities of reporter proteins were determined using corresponding assay systems according to the manufacturer's instructions.

For the SEAP assay, 5 µL of each of the culture media was transferred to another 384-well plate and incubated with 55 µL of the SEAP assay mixture (EscAPe SEAP Chemiluminescent Assay System, Clontech Laboratories) at room temperature for 20 minutes. SEAP activity was measured using a luminescent reader (Wallac VICTOR$^2$, PerkinElmer Life Sciences).

The Dual Luciferase Reporter Assay System (Promega) was used for FL and RL assays. In the original 384-well culture plate, the remaining media was removed, and the cells were washed once with 40 µL of phosphate buffer-saline (PBS). The washed cells were incubated with Passive Lysis Buffer (PLB, 5 µL/well) for 20 minutes at room temperature with mild-shaking. Then, the Luciferase Assay Reagent II (LAR II, 25 µL/well) was added directly to the cell lysates, and FL activity was determined using a luminescent reader (Wallac VICTOR$^2$, PerkinElmer Life Sciences). After measuring the FL activity, Stop & Glo Reagent (25 μL/well) was added, and the RL activity was determined. In the screens, chemical compounds were identified that specifically affected p53-dependent FL and SEAP expression, without affecting CMV promoter-driven RL expression.

Example 2—Double Readout Assay for p53 Protein Stability

Figure 6:
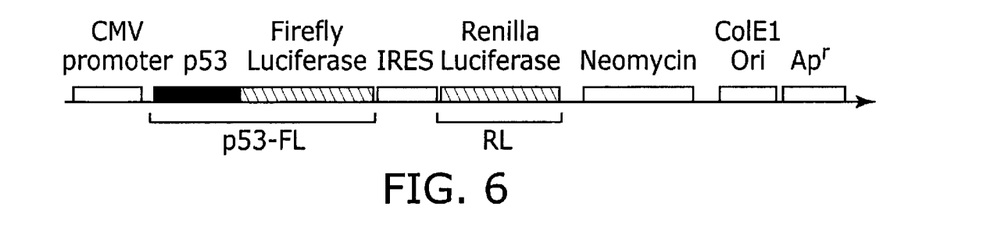
FIG. 6 shows a reporter plasmid used for p53 protein stability and levels. The p53 gene was fused with FL (firefly luciferase) reporter gene. p53-FL fusion protein was expressed together with RL (renilla luciferase) reporter protein through IRES (internal ribosome entry site) under the control of CMV promoter. This reporter plasmid was used to monitor the stability of p53 protein in cells.
Figure 7:
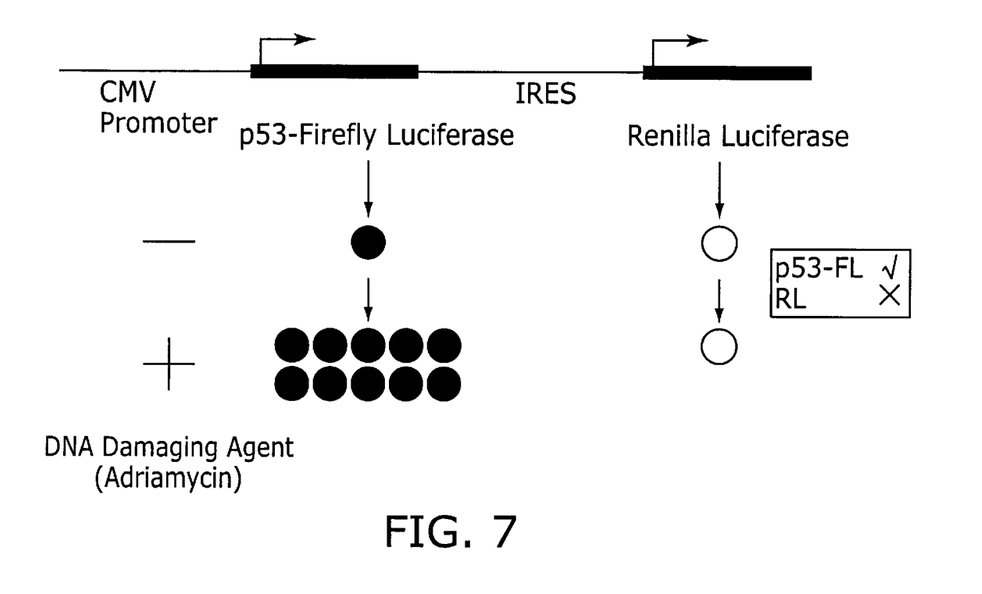
Figure 8A:
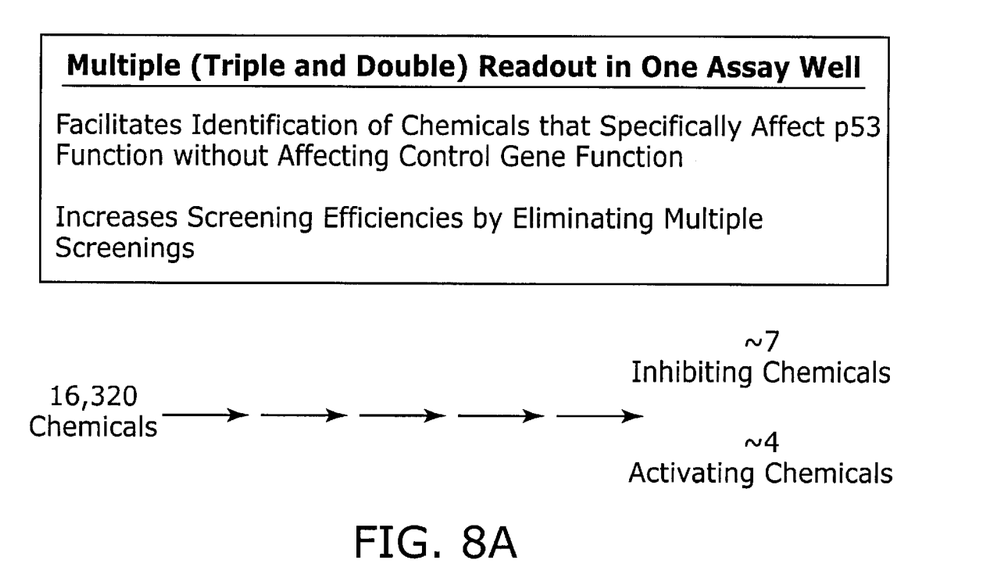
Figure 8B:
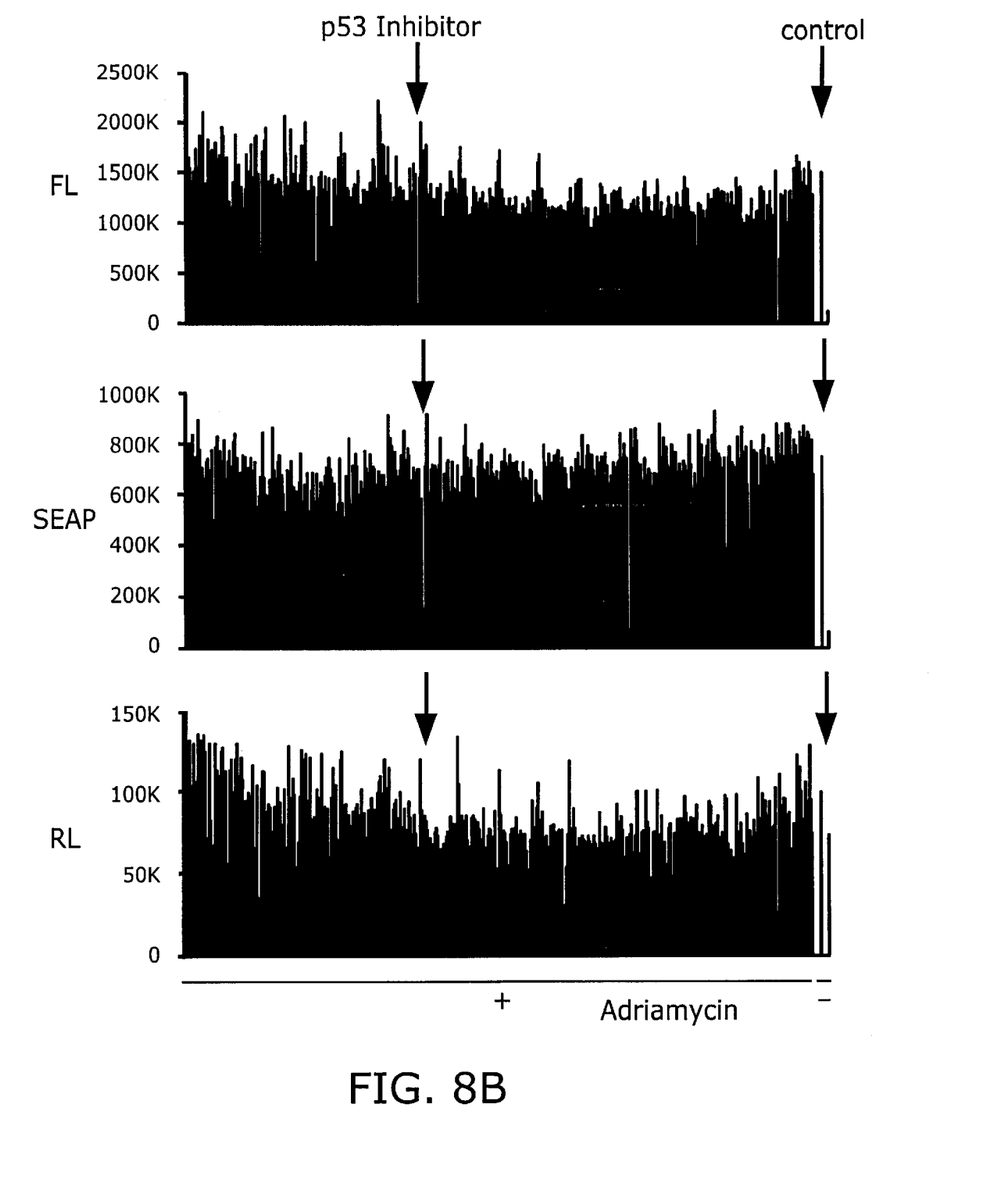
Figure 9:
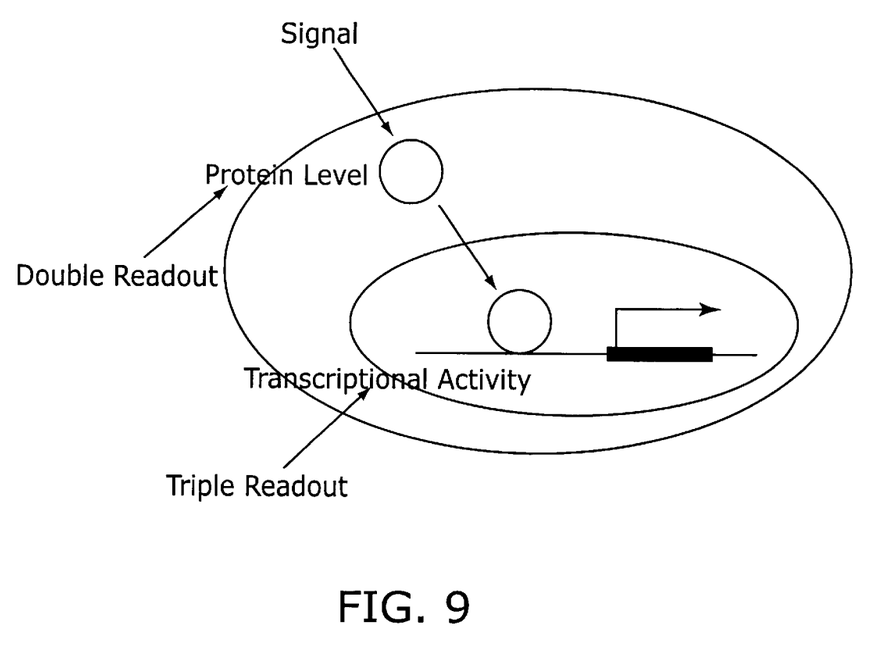

A plasmid expressing both the p53/FL fusion gene and RL gene under the control of a single CMV promoter with an internal ribosome entry site (IRES) was created (see FIG. 6). Co-expression of p53/FL and RL proteins by taking advantage of the internal ribosome entry site makes it possible to normalize the levels of p53/FL with those of RL in various assay conditions. The reporter cell line was established by selecting MCF7 cells tranfected with the IRES expression plasmid using media containing Geneticin (G418) (700 μg/mL). In the screen, the activities of the two different reporter proteins, p53/FL and RL, were measured to determine the effect of the test chemical compounds.

Cells derived from the reporter cell line were maintained in DMEM media supplemented with antibiotics and 10% FBS. After monomerization of reporter cells with trypsin treatment, an equal number of cells in 30 μL volume was dispensed in each well of a 384-well plate ($5\times10^3$ cells/well) using an automatic dispenser (Multidrop 384, Labsystems). After 12–16 hours, test chemical compounds were introduced in the wells using pin arrays at a final concentration of ~5 μg/mL of the test compound and pre-incubated with the cells for 2 hours, followed by the addition of adriamycin (1.0 μM).

After 24 hours, activities of p53/FL and RL were determined in the same wells using the Dual Luciferase Reporter Assay System (Promega). In the 384-well culture plate, the remaining media was removed from the cells, and the cells were washed once with 40 μL of PBS. The washed cells were then incubated with Passive Lysis Buffer (PLB, 5 μL/well) for 20 minutes at room temperature with mild shaking. After the Luciferase Assay Reagent II (LAR II, 25 μL/well) was added directly to the cell lysates, FL activity was measured using a luminescence reader (Wallac VICTOR$^2$, PerkinElmer Life Sciences). The Stop & Glo Reagent (25 μL/well) was then added to determine the RL activity. In the screen, test chemical compounds were identified that specifically affect the stabilization of p53-FL without affecting that of RL. The observed effects of these chemical compounds were confirmed by immunoblot analyses of endogenous p53 protein and other endogenous control proteins such as actin.

Other Embodiments

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

What is claimed is:

1. A method of identifying compounds that affect the transcription of genes regulated by p53, the method comprising the steps of:
   providing a first cell line containing a construct comprising a p53 binding element operably linked to a first reporter gene;
   providing a second cell line that differs from said first cell line in that it contains a construct comprising a p53 binding element operably linked to a second reporter gene;
   providing a third cell line that differs from said first cell line in that it contains a construct comprising a promoter operably linked to a third reporter gene;
   contacting a test compound with cells from each of the three cell lines; and
   determining effect of the test compound on expression of the three reporter genes.

2. A method of identifying compounds that affect the transcription of genes regulated by p53, the method comprising the steps of:
   providing a first cell line containing a construct comprising a p53 binding element operably linked to a first reporter gene;
   providing a second cell line that differs from said first cell line in that it contains a construct comprising a p53 binding element operably linked to a second reporter gene;
   contacting a test compound with cells from each of the two cell lines; and
   determining effect of the test compound on expression of the reporter genes.

3. The method of claim 1 or 2 wherein the cell line is a cell line that has detectable induction of p53 after treatment with a DNA damaging agent.

4. The method of claim 1 or 2 wherein the cell line is a cell line that expresses wild type p53.

5. The method of claim 1 or 2 wherein the cell line is a cell line that has intact p53-mediated growth arrest pathways in response to DNA damage.

6. The method of claim 1 or 2 wherein the cell line is an animal cell line.

7. The method of claim 1 or 2 wherein the cell line is a mammalian cell line.

8. The method of claim 1 or 2 wherein the cell line is a human cell line.

9. The method of claim 1 or 2 wherein the cell line is RKO cell line.

10. The method of claim 1 or 2 wherein the p53 binding element is the p53 binding element found in a p21 gene.

11. The method of claim 1 or 2 wherein the p53 binding element is the p53 binding element found in a bax gene.

12. The method of claim 1 or 2 wherein the p53 binding element is the p53 binding element found in a 14-3-3- gene.

13. The method of claim 1 or 2 wherein the p53 binding element comprises multiple p53 binding sites.

14. The method of claim 1 wherein the promoter is a constitutive promoter.

15. The method of claim 1 wherein the promoter is a CMV promoter.

16. The method of claim 1 wherein the first, second, or third reporter gene is selected from the group consisting of firefly luciferase, secreted alkaline phosphatase, enhanced green fluorescent protein, horseradish peroxidase, and renilla luciferase.

17. The method of claim 1 wherein the first, second, or third reporter gene is selected from the group consisting of firefly luciferase, secreted alkaline phosphatase, renilla luciferase, and β-galactosidase.

18. The method of claim 1 wherein the first, second, or third reporter gene encodes a protein detectable by an antibody.

19. The method of claim 1 wherein the first, second, or third reporter gene encodes a gene product detectable by a change in absorbance, change in fluorescence, or radio-immuno assay.

20. A kit useful in identifying compounds that affect the transcription of genes regulated by p53 comprising:
   a first cell line with a construct comprising a p53 binding element operably linked to a first reporter gene;
   a second cell line with a construct comprising a p53 binding element operably linked to a second reporter gene; and
   a third cell line with a construct comprising a promoter operably linked to a third reporter gene.

21. The method of claim 1 wherein the first, second, and third reporter gene is selected from the group consisting of firefly luciferase, secreted alkaline phosphatase, enhanced green fluorescent protein, horseradish peroxidase, and renilla luciferase.

22. The method of claim 1 wherein the first, second, and third reporter gene is selected from the group consisting firefly luciferase, secreted alkaline phosphatase, renilla luciferase, and β-galactosidase.

23. The method of claim 1 wherein the first, second, and third reporter gene encodes a protein detectable by an antibody.

24. The method of claim 1 wherein the first, second, and third reporter gene encodes a gene product detectable by a change in absorbance, change in fluorescence, or radio-immuno assay.

25. The method of claim 2 wherein the first or second reporter gene is selected from the group consisting of firefly luciferase, secreted alkaline phosphatase, enhanced green fluorescent protein, horseradish peroxidase, and renilla luciferase.

26. The method of claim 2 wherein the first or second reporter gene is selected from the group consisting of firefly luciferase, secreted alkaline phosphatase, renilla luciferase, and β-galactosidase.

27. The method of claim 2 wherein the first or second reporter gene encodes a protein detectable by an antibody.

28. The method of claim 2 wherein the first or second reporter gene encodes a gene product detectable by a change in absorbance, change in fluorescence, or radio-immuno assay.

29. The method of claim 2 wherein the first and second reporter gene is selected from the group consisting of firefly luciferase, secreted alkaline phosphatase, enhanced green fluorescent protein, horseradish peroxidase, and renilla luciferase.

30. The method of claim 2 wherein the first and second reporter gene is selected from the group consisting of firefly luciferase, secreted alkaline phosphatase, renilla luciferase, and β-galactosidase.

31. The method of claim 2 wherein the first and second reporter gene encodes a protein detectable by an antibody.

32. The method of claim 2 wherein the first and second reporter gene encodes a gene product detectable by a change in absorbance, change in fluorescence, or radio-immuno assay.

* * * * *